United States Patent
Bae et al.

(10) Patent No.: US 12,370,277 B2
(45) Date of Patent: Jul. 29, 2025

(54) LED LIGHTING APPARATUS HAVING STERILIZING FUNCTION

(71) Applicant: SEOUL VIOSYS CO., LTD., Ansan-si (KR)

(72) Inventors: Hee Ho Bae, Ansan-si (KR); A Young Lee, Ansan-si (KR); Yeong Min Yoon, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 0 days.

(21) Appl. No.: 18/581,047

(22) Filed: Feb. 19, 2024

(65) Prior Publication Data
US 2024/0189465 A1    Jun. 13, 2024

Related U.S. Application Data

(63) Continuation of application No. 18/074,516, filed on Dec. 5, 2022, now Pat. No. 11,904,059, which is a
(Continued)

(51) Int. Cl.
*A61L 2/08*    (2006.01)
*A61L 2/24*    (2006.01)
(Continued)

(52) U.S. Cl.
CPC .............. *A61L 2/084* (2013.01); *A61L 2/24* (2013.01); *F21K 9/62* (2016.08); *H01L 25/0753* (2013.01);
(Continued)

(58) Field of Classification Search
CPC ........ A61L 2/084; A61L 2/24; A61L 2202/14; A61L 2202/11; A61L 9/20;
(Continued)

(56) References Cited

U.S. PATENT DOCUMENTS

| | | |
|---|---|---|
| 8,071,988 B2 | 12/2011 | Lee et al. |
| 9,927,097 B2 | 3/2018 | Lalicki et al. |

(Continued)

FOREIGN PATENT DOCUMENTS

| | | |
|---|---|---|
| KR | 10-2005-0106945 | 11/2005 |
| KR | 10-2016-0025223 | 3/2016 |

(Continued)

OTHER PUBLICATIONS

Non-Final Office Action dated Jun. 16, 2021, in U.S. Appl. No. 16/697,500.

(Continued)

*Primary Examiner* — Kevin Quarterman
(74) *Attorney, Agent, or Firm* — Oblon, McClelland, Maier & Neustadt, L.L.P.

(57) ABSTRACT

A light emitting apparatus including a first light emitter including at least one first light emitting diode and a wavelength converter, and a second light emitter including at least one second light emitting diode, in which the first light emitting diode emits light having a central wavelength in a range of violet or blue, the second light emitting diode emits light having a central wavelength in a range of about 400 nm to 420 nm, the wavelength converter includes green and red phosphors to convert light of the first light emitting diode into the white light, in the white light, an irradiance of light emitted from the first light emitting diode is less than that from the red phosphor, and an irradiance of light emitted from the second light emitting diode is greater than that of the white light emitted from the first light emitter at the same wavelength.

20 Claims, 9 Drawing Sheets

Related U.S. Application Data continuation of application No. 17/676,768, filed on Feb. 21, 2022, now Pat. No. 11,517,635, which is a continuation of application No. 16/697,500, filed on Nov. 27, 2019, now Pat. No. 11,253,618.

(60) Provisional application No. 62/773,138, filed on Nov. 29, 2018.

(51) Int. Cl.
*F21K 9/62* (2016.01)
*H01L 25/075* (2006.01)
*H10H 20/851* (2025.01)
*H10H 20/857* (2025.01)
*F21Y 113/00* (2016.01)
*F21Y 115/10* (2016.01)

(52) U.S. Cl.
CPC .... *H10H 20/8514* (2025.01); *H10H 20/8515* (2025.01); *H10H 20/857* (2025.01); *A61L 2202/11* (2013.01); *A61L 2202/14* (2013.01); *F21Y 2113/30* (2023.05); *F21Y 2115/10* (2016.08)

(58) Field of Classification Search
CPC ... H01L 25/0753; H01L 33/62; H01L 33/507; H01L 33/505; H01L 33/504; H01L 33/502; F21K 9/62; H05B 45/10; H05B 45/20; F21Y 2115/10; F21Y 2113/13
See application file for complete search history.

(56) References Cited

U.S. PATENT DOCUMENTS

| | | |
|---|---|---|
| 10,309,614 B1 | 6/2019 | Jones et al. |
| 10,617,774 B2 | 4/2020 | Winslow et al. |
| 11,904,059 B2 * | 2/2024 | Bae .................. H01L 33/504 |
| 2016/0030610 A1 | 2/2016 | Peterson et al. |
| 2016/0375161 A1 | 12/2016 | Hawkins et al. |
| 2017/0080116 A1 | 3/2017 | Kreiner et al. |
| 2017/0250319 A1 | 8/2017 | Yajima et al. |
| 2017/0368210 A1 | 12/2017 | David et al. |

FOREIGN PATENT DOCUMENTS

| | | |
|---|---|---|
| KR | 10-1680488 | 11/2016 |
| KR | 10-2018-0036728 | 4/2018 |
| KR | 10-2018-0054183 | 5/2018 |
| KR | 10-1892996 | 8/2018 |

OTHER PUBLICATIONS

Notice of Allowance dated Oct. 13, 2021, in U.S. Appl. No. 16/697,500.

Extended European Search Report dated Jul. 21, 2022, issued in European Patent Application No. 19888827.3.

Notice of Allowance dated Oct. 6, 2022, issued to U.S. Appl. No. 17/676,768.

Extended European Search Report issued Jun. 11, 2024 in European Patent Application No. 24150129.5, 10 pages.

* cited by examiner (a)

(b)

(c)

(d)

LED LIGHTING APPARATUS HAVING STERILIZING FUNCTION

CROSS-REFERENCE TO RELATED APPLICATIONS

This application is a Continuation of U.S. patent application Ser. No. 18/074,516, filed on Dec. 5, 2022, which is a Continuation of U.S. patent application Ser. No. 17/676,768, filed on Feb. 21, 2022, which is a Continuation of U.S. patent application Ser. No. 16/697,500, filed on Nov. 27, 2019, which claims the benefit of U.S. Provisional Application No. 62/773,138, filed on Nov. 29, 2018, each of which is hereby incorporated in its entirety by reference for all purposes as set forth herein.

BACKGROUND

Field

Exemplary embodiments relate to a lighting apparatus having a sterilizing function using LEDs.

Discussion of the Background

As an inorganic light source, light emitting diodes have been used in various fields including displays, vehicular lamps, general lighting, and the like. In particular, with various advantages, such as long lifespan, low power consumption, and rapid response, light emitting diodes have been replacing existing light sources.

Sunlight exhibits a broad spectrum of wavelengths in the ultraviolet, visible, and infrared regions. It is well known that ultraviolet rays have a sterilizing function. Accordingly, various light sources having the sterilizing function using ultraviolet LEDs have been developed. However, ultraviolet rays with the sterilizing function are generally harmful to the human body, particularly to the human eyes or skin. For this reason, light sources using ultraviolet LEDs are subject to restrictions and must be used in a space without people. More particularly, ultraviolet LEDs with the sterilizing function are not generally suitable for use in lighting apparatuses in places where people are active.

The above information disclosed in this Background section is only for understanding of the background of the inventive concepts, and, therefore, it may contain information that does not constitute prior art.

SUMMARY

Exemplary embodiments provide a lighting apparatus having a sterilizing function without harming the human body, such as causing eye diseases or skin diseases, and a lighting system having the same.

Exemplary embodiments also provide a lighting apparatus capable of changing color temperature over time like sunlight, and having a sterilizing function and a lighting system having the same.

Exemplary embodiments further provide a lighting apparatus capable of changing color temperature in consideration of the color temperature of sunlight according to a region and time and having a sterilization function, and a lighting system having the same.

Additional features of the inventive concepts will be set forth in the description which follows, and in part will be apparent from the description, or may be learned by practice of the inventive concepts.

A lighting apparatus according to an exemplary embodiment includes: a white light emitting device including at least one first light emitting diode and a wavelength converter to implement white light; and at least one second light emitting diode emitting light suitable for sterilizing at least one pathogenic microorganism, in which the first light emitting diode emits light having a central wavelength in a range of about 300 nm to about 420 nm, the second light emitting diode emits light having a central wavelength in a range of about 400 nm to about 420 nm, the wavelength converter includes a plurality of wavelength conversion substances to convert light of the first light emitting diode into white light, the lighting apparatus emits the white light implemented in the white light emitting device and light generated by the second light emitting diode to the outside, and, in irradiance spectrum of the white light implemented in the white light emitting device, irradiance of the central wavelength of light emitted from the first light emitting diode is smaller than that of a peak wavelength of blue light emitted from a blue wavelength conversion substance of the wavelength conversion substances.

As used herein, sterilization may refer to killing or damaging a pathogenic microorganism so as to reduce or prevent the growth of the pathogenic microorganism.

The lighting apparatus having a sterilizing function may be provided by using the second light emitting diode suitable for sterilizing pathogenic microorganisms together with the white light emitting device. Since irradiance of light emitted from the first light emitting diode is smaller than that of the peak wavelength of blue light emitted from the blue wavelength conversion substance, the lighting apparatus may prevent the first light emitting diode from causing harm to the human body or from causing eye diseases or skin diseases.

The wavelength converter may include wavelength conversion substances for converting light of the first light emitting diode into blue, green, and red light.

The wavelength converter may include blue and orange wavelength conversion substances for converting light of the first light emitting diode into blue and orange light.

The white light and light emitted from the second light emitting diode may be mixed and emitted. For example, the lighting apparatus may further include a diffusion plate for mixing the white light and light emitted from the second light emitting diode.

The second light emitting diode may emit light having a central wavelength of about 405 nm. The wavelength of 405 nm may be suitable for sterilizing pathogenic microorganisms without causing eye diseases or skin diseases in the visible region.

The wavelength converter may include a phosphor or a quantum dot. For example, the wavelength converter may include a blue phosphor, a green phosphor, and a red phosphor. At least some of the phosphors may be replaced with quantum dots.

Light emitted from the second light emitting diode may be emitted to the outside without passing through the wavelength converter. A portion of light emitted from the second light emitting diode may be wavelength-converted by the wavelength converter.

Irradiance of light generated by the at least one second light emitting diode and emitted to the outside may be greater than that of light generated by the at least one first light emitting diode and emitted to the outside without wavelength conversion. Accordingly, pathogenic microorganisms may be sterilized using the second light emitting diode.

The lighting apparatus may include a greater number of first light emitting diodes than that of the at least one second light emitting diode. Accordingly, the irradiance of the white light emitting device may be greater than that of the second light emitting diode.

Irradiance of light generated by the at least one second light emitting diode and emitted to the outside may be smaller than or equal to 1 W/m².

The lighting apparatus may further include a circuit board on which the first light emitting diode and the second light emitting diode may be mounted.

The first light emitting diode may emit light having a central wavelength in a range of about 400 nm to about 420 nm. The first light emitting diode may emit light having a central wavelength of about 405 nm. In this case, a portion of light emitted from the first light emitting diode may be emitted to the outside without wavelength conversion to sterilize pathogenic microorganisms. In particular, when the white light emitting device implements white light of 6500K, since irradiance of light of the central wavelength emitted from the first light emitting diode in the white light is relatively large compared to white light of other color temperatures, the pathogenic microorganisms may be sterilized using the white light emitting device without using the second light emitting diode. As such, in this case, the second light emitting diode may be omitted.

Furthermore, since the irradiance of light of the central wavelength emitted from the first light emitting diode changes according to a color temperature of white light implemented by the white light emitting device, according to the change in the irradiance, irradiance of the light emitted from the second light emitting diode may be changed to provide irradiance suitable for sterilizing the pathogenic microorganisms.

The lighting apparatus may include a location information receiver for receiving location information; and a controller for receiving the location information from the location information receiver and controlling a dose of light emitted from the white light emitting device; in which the controller may calculate a dose of light to be emitted by the white light emitting device based on the location information, and may control the white light emitting device to emit light in an amount equivalent to the dose.

The controller may calculate an appropriate dose based on the location information provided by the location information receiver, and may control the light source to emit the appropriate dose.

The location information receiver may calculate location information of the lighting apparatus, the controller may receive the location information and calculate a dose of external light and an appropriate dose at the place where the lighting apparatus is located, and may control the white light emitting device to emit light in an amount equivalent to a difference between the appropriate dose and the dose of external light.

The controller may calculate time information from the location information and may control a dose of light to be emitted by the white light emitting device according to the time information.

A lighting apparatus according to another exemplary embodiment includes: a first light emitting unit including a first first-light emitting diode emitting light having a central wavelength in a range of about 300 nm to about 420 nm and a first wavelength converter; a second light emitting unit including a first second-light emitting diode emitting light having a central wavelength in a range of about 300 nm to about 420 nm and a second wavelength converter; a third light emitting unit including a first third-light emitting diode emitting light having a central wavelength in a range of about 300 nm to about 420 nm and a third wavelength converter, at least one second light emitting diode emitting light having a central wavelength in a range of about 400 nm to about 420 nm; in which the first to third wavelength converters include a blue wavelength conversion substance for converting light emitted from the light emitting diode into blue light, respectively, and, in irradiance spectrum of light emitted to the outside, irradiance of the central wavelength of light generated by each light emitting diode in the first to third light emitting units and emitted to the outside without wavelength conversion is smaller than that of a peak wavelength of blue light emitted from the corresponding respective wavelength converters in the first to third light emitting units.

The lighting apparatus may include a plurality of light emitting units, thereby implementing white light having various color temperatures.

The first to third wavelength converters may further include a green wavelength conversion substance for converting light emitted from the first light emitting diode into green light, and a red wavelength conversion substance for converting light emitted from the first light emitting diode into red light, respectively. Accordingly, the first to third light emitting units may implement white light, respectively.

The first first- to first third-light emitting diodes may emit light having a central wavelength in a range of about 400 nm to about 420 nm. The first first- to first third-light emitting diodes may emit light having the same peak wavelength.

Light wavelength-converted by the wavelength converter and light emitted from the second light emitting diode may be mixed and emitted to the outside. The mixed light may be white light.

The lighting apparatus may further include a diffusion plate suitable for mixing light wavelength-converted by the wavelength converter and light emitted from the second light emitting diode.

The first light emitting unit, the second light emitting unit, and the third light emitting unit may emit white light having different color temperatures. In addition, the first light emitting unit, the second light emitting unit, and the third light emitting unit may be driven independently of one another.

Accordingly, the lighting apparatus may change the color temperature in accordance with the change of sunlight over time.

The first first- to first third-light emitting diodes may be disposed more than the at least one second light emitting diode, respectively.

The lighting apparatus may further include a circuit board on which the first first-to first third-light emitting diodes and the second light emitting diode are mounted.

The lighting apparatus may further include a location information receiver for receiving location information, and a controller for controlling a dose of light emitted from the first to third light emitting units, in which the controller may control the dose of light emitted from the first to third light emitting units based on the location information.

The controller may calculate an appropriate dose based on the location information provided by the location information receiver, and may control the first to third light emitting units to emit the appropriate dose.

The location information receiver may calculate location information of the lighting apparatus, the controller may receive the location information and calculate a dose of external light and an appropriate dose at the place where the lighting apparatus is located, and may control the first to third light emitting units to emit light in an amount equivalent to a difference between the appropriate dose and the dose of external light.

The controller may calculate time information from the location information and may control a dose of the light according to the time information.

A lighting system according to an exemplary embodiment includes a lighting apparatus installed indoors, in which the lighting apparatus is one of the lighting apparatuses described above.

It is to be understood that both the foregoing general description and the following detailed description are exemplary and explanatory and are intended to provide further explanation of the invention as claimed

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

DETAILED DESCRIPTION

Figure 1:
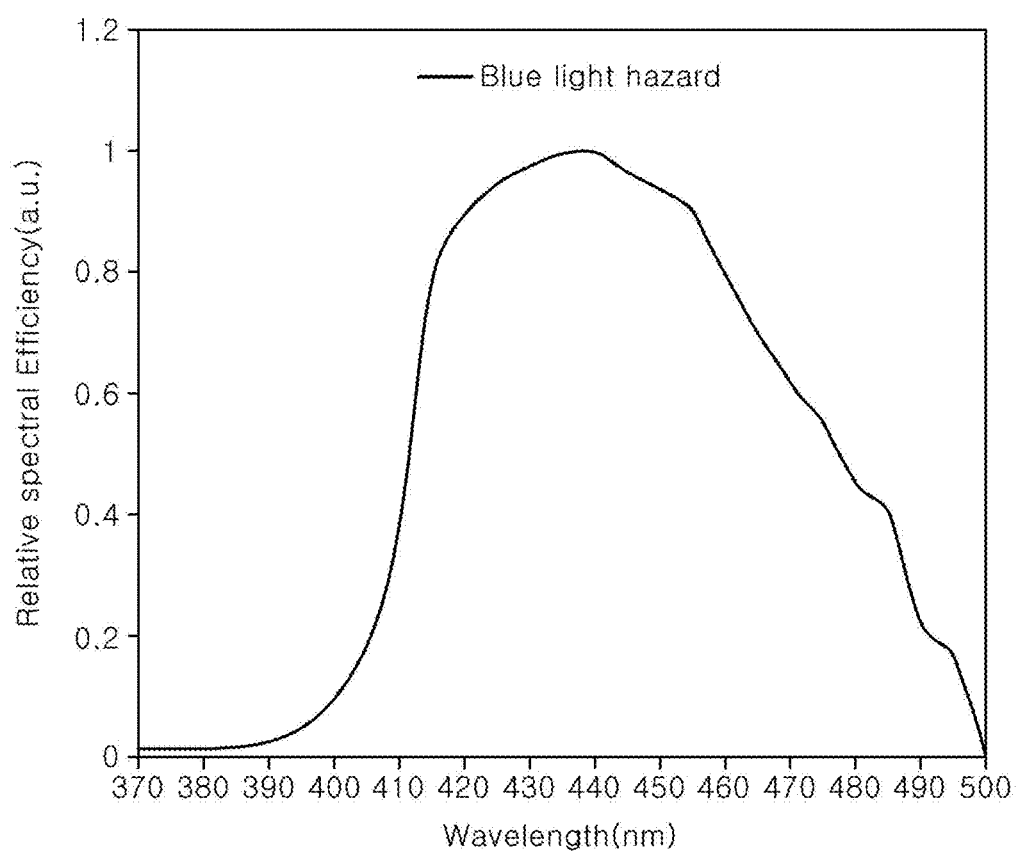
FIG. 1 is a graph showing a degree of hazard according to wavelengths of blue light.

Hereinafter, exemplary embodiments of the present disclosure will be described in detail with reference to the accompanying drawings. The following embodiments are provided by way of example so as to fully convey the spirit of the present disclosure to those skilled in the art to which the present disclosure pertains. Accordingly, the present disclosure is not limited to the embodiments disclosed herein and can also be implemented in different forms. In the drawings, widths, lengths, thicknesses, and the like of elements can be exaggerated for clarity and descriptive purposes. When an element or layer is referred to as being "disposed above" or "disposed on" another element or layer, it can be directly "disposed above" or "disposed on" the other element or layer or intervening elements or layers can be present. Throughout the specification, like reference numerals denote like elements having the same or similar functions.

Hereinafter, exemplary embodiments will be described in detail with reference to the accompanying drawings.

FIG. 1 is a graph showing a degree of hazard according to wavelengths of blue light.

Blue light is known to cause eye diseases and skin diseases. In particular, blue light exhibits the highest degree of hazard between 430 nm and 440 nm. A wavelength range of 420 nm to 455 nm exhibits about 90% or more degree of hazard with respect to the highest hazard value, and a wavelength range of 413 nm to 465 nm exhibits about 70% or more degree of hazard, and a wavelength range of 411 nm to 476 nm exhibits about 50% or more degree of hazard.

In addition, ultraviolet rays is also known to harm the human body and exhibit the highest degree of hazard, especially between 270 nm and 280 nm.

Figure 2:
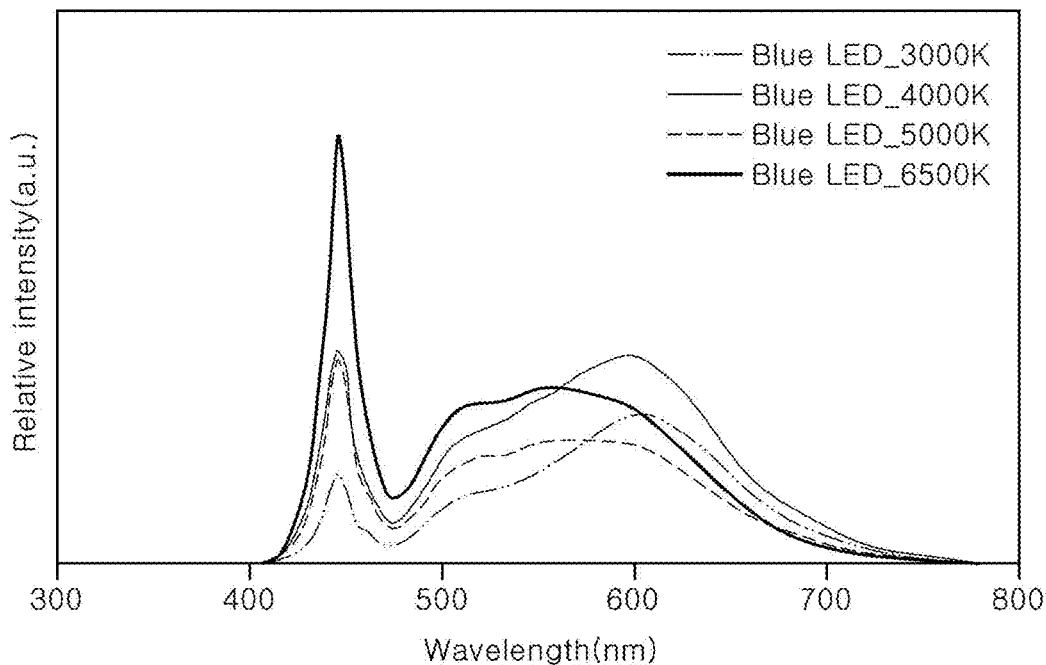
FIG. 2 shows a spectrum of a conventional white light source using a blue light emitting diode.

FIG. 2 shows a spectrum of a conventional white light source using a blue light emitting diode.

Referring to FIG. 2, a conventional white light source may implement white light using a yellow phosphor, or a green phosphor and a red phosphor, together with a blue light emitting diode. A type and the amount of the phosphor may be controlled according to a desired color temperature, and an intensity of the blue light is increased as the desired color temperature is increased.

A blue light emitting diode used in the conventional white light source generally has a central wavelength (e.g., a peak wavelength) in a range of 430 nm to 470 nm. Blue light in this range has a relatively high degree of hazard as shown in FIG. 1. As such, as the color temperature of the white light source increases, the intensity of the blue light increases, thereby increasing the hazard of causing eye diseases or skin diseases.

Figure 3:
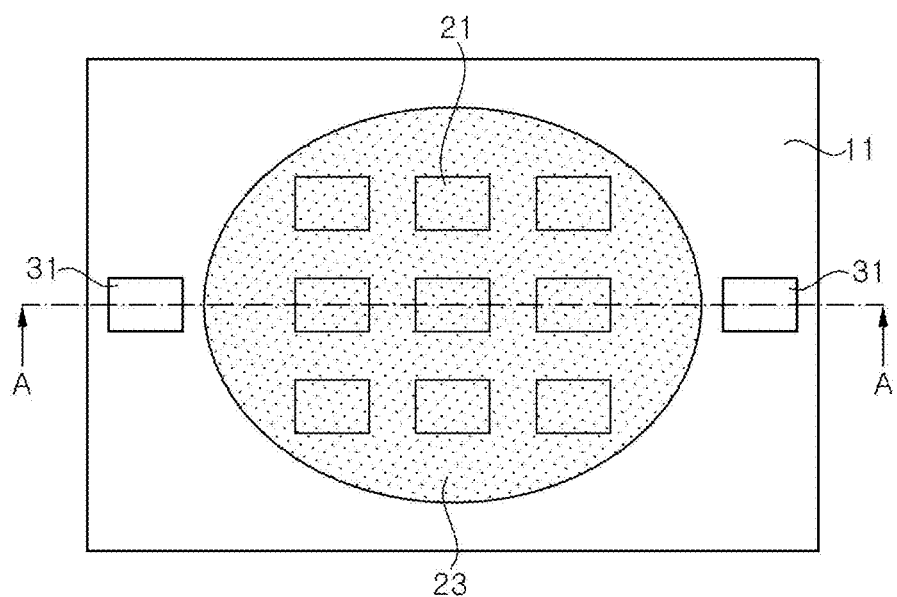
FIG. 3 is a schematic plan view illustrating a lighting apparatus according to an exemplary embodiment.
Figure 4:
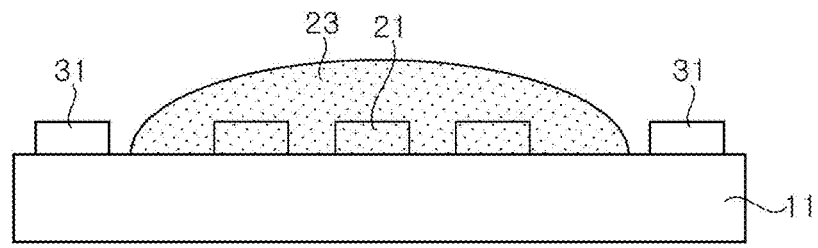
FIG. 4 is a schematic cross-sectional view taken along line A-A of FIG. 3.

FIG. 3 is a schematic plan view illustrating a lighting apparatus according to an exemplary embodiment, and FIG. 4 is a schematic cross-sectional view taken along line A-A of FIG. 3.

Referring to FIG. 3 and FIG. 4, the lighting apparatus may include a circuit board 11, a first light emitting diode 21, a wavelength converter 23, and a second light emitting diode 31.

The circuit board 11 may have a circuit pattern for supplying power to the first and second light emitting diodes 21 and 31. The circuit board 11 may be a printed circuit board, for example, a metal-PCB.

At least one first light emitting diode 21 is mounted on the circuit board 11 as a light source for implementing white light. A plurality of first light emitting diodes 21 may be electrically connected to one another in various ways, for example, may be connected in series, in parallel, or in series parallel.

The first light emitting diode 21 may have, for example, a central wavelength in a range of about 300 nm to 420 nm, and in some exemplary embodiments, in a range of 400 nm to 420 nm. When the first light emitting diode 21 has the central wavelength in this range, a substantial portion of light emitted from the first light emitting diode 21 may be wavelength-converted by the wavelength converter 23. When the first light emitting diode 21 emits ultraviolet rays, most of ultraviolet rays are wavelength-converted by the wavelength converter 23, thereby preventing ultraviolet rays from being emitted to the outside. Furthermore, when the first light emitting diode having the center wavelength in the range of 400 nm to 420 nm is used, safety problems that may otherwise be caused by ultraviolet rays may be eliminated in advance.

The wavelength converter 23 converts a wavelength of light emitted from the first light emitting diode 21. The wavelength converter 23 may be, for example, a molding member including a phosphor or a quantum dot. The wavelength converter 23 may cover the first light emitting diode 21. When the plurality of first light emitting diodes 21 are mounted on the circuit board 11, the wavelength converter 23 may cover each of the plurality of first light emitting diodes 21.

The wavelength converter 23 includes a wavelength conversion substance for implementing white light together with light of the first light emitting diode 21. In one exemplary embodiment, the wavelength converter 23 may include a blue phosphor, a green phosphor, and a red phosphor. In another exemplary embodiment, the wavelength converter 23 may include a blue phosphor and an orange phosphor. In another exemplary embodiment, the wavelength converter may include a quantum dot.

The blue phosphor may include a BAM-based, a halophosphate-based, or an aluminate-based phosphor, and may include, for example, $BaMgAl_{10}O_{17}:Mn^{2+}$, $BaMgAl_{12}O_{19}:Mn^{2+}$ or $(Sr,Ca,Ba)PO_4Cl:Eu^{2+}$. The blue phosphor may have, for example, a peak wavelength in a range of 440 nm to 500 nm.

The green phosphor may include $LuAG(Lu_3(Al,Gd)_5O_{12}:Ce^{3+})$, $YAG(Y_3(Al,Gd)_5O_{12}:Ce^{3+})$, $Ga-LuAG((Lu,Ga)_3(Al,Gd)_5O_{12}:Ce^{3+})$, $Ga-YAG$ $((Ga, Y)_3(Al,Gd)_5O_{12}:Ce^{3+})$, $LuYAG$ $((Lu,Y)_3(Al,Gd)_5O_{12}:Ce^{3+})$, ortho-silicate $((Sr,Ba,Ca,Mg)_2SiO_4:Eu^{2+})$, oxynitride $((Ba,Sr,Ca)Si_2O_2N_2:Eu^{2+})$, or thio gallate $(SrGa_2S_4:Eu^{2+})$. The green phosphor may have a peak wavelength in a range of 500 nm to 600 nm.

The red phosphor may include a nitride-based, a sulfide-based, a fluoride or an oxynitride-based phosphor, and, specifically, may include $CASN(CaAlSiN_3:Eu^{2+})$, $(Ba,Sr,Ca)_2Si_5N_8:Eu^{2+}$, $(Ca,Sr)S_2:Eu^{2+}$, or $(Sr,Ca)_2SiS_4:Eu^{2+}$. The red phosphor may have a peak wavelength in a range of 600 nm to 700 nm.

Figure 5:
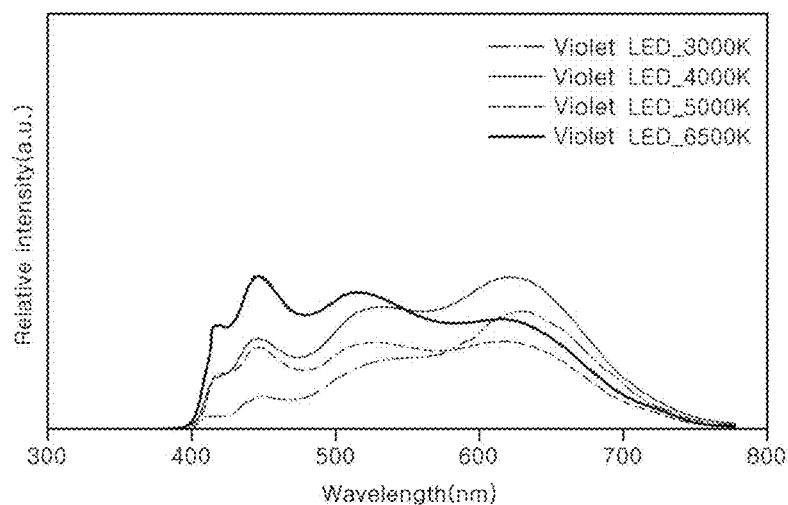
FIG. 5 shows representative spectra of a lighting apparatus according to an exemplary embodiment.

White light may be implemented by a combination of the first light emitting diode 21 and the wavelength converter 23. FIG. 5 shows spectra of white light having various color temperatures implemented by the combination of the first light emitting diode 21 and the wavelength converter 23.

As shown in FIG. 5, white light of each color temperature is implemented by the combination of light emitted from the first light emitting diode and light emitted from the phosphors. In addition, it can be confirmed that irradiance of light emitted from the first light emitting diode 21 at all color temperatures is less than that of light emitted from the blue phosphor. As the color temperature increases, although the irradiance of light emitted from the first light emitting diode 21 also increases, the irradiance of blue light emitted from the blue phosphor increases to a greater extent. In addition, the irradiance of light emitted from the first light emitting diode 21 may be less than that of light emitted from the green phosphor and less than that of light emitted from the red phosphor.

Accordingly, the lighting apparatus may prevent eye diseases or skin diseases by light emitted from the first light emitting diode 21.

Referring back to FIG. 3 and FIG. 4, the second light emitting diode 31 may be spaced apart from the wavelength converter 23 and is mounted on the circuit board 11. Light emitted from the second light emitting diode 31 may be emitted to the outside without actually entering the wavelength converter 23. Accordingly, irradiance of light emitted from the second light emitting diode 31 may be improved.

The second light emitting diode 31 may be connected to the first light emitting diode 21 in series or in parallel, or may be driven independently from the first light emitting diode 21.

The second light emitting diode 31 emits light suitable for sterilizing pathogenic microorganisms other than the white light. The second light emitting diode 31 may emit light having, for example, a central wavelength of about 400 nm to about 420 nm, furthermore, a central wavelength of about 400 nm to about 410 nm, even furthermore, a central wavelength of about 405 nm. Although ultraviolet light has a favorable sterilization capability, ultraviolet light cannot generally be used indoors or in public places where people are active as being harmful to the human body. However, visible light of the short wavelength in the range of 400 nm to 420 nm is a relatively low hazard of eye diseases or skin diseases, and has a high sterilization capability, and thus, it may be suitably used in the lighting apparatus.

Furthermore, since light in the range of 400 nm to 420 nm is similar to light emitted from the first light emitting diode 21, the second light emitting diode 31 may be efficiently used in the lighting apparatus employing the first light emitting diode 21.

In order to add the sterilizing function to the lighting apparatus, the irradiance of light emitted from the second light emitting diode 31 may be greater than that from the white light emitting device at the same wavelength. Furthermore, the irradiance of light emitted from the second light emitting diode 31 may be greater than that emitted to the outside of the lighting apparatus from the first light emitting diode 21 having the central wavelength in the range of 300 nm to 420 nm. Accordingly, the second light emitting diode 31 may provide a substantial sterilizing function in the lighting apparatus, as compared to the first light emitting diode 21.

According to an exemplary embodiment, a driving time of the second light emitting diode 31 and that of the first light emitting diode 21 may be the same. However, the inventive concepts are not limited thereto, and in some exemplary embodiments, the driving time of the second light emitting diode 31 may be adjusted according to an installation location of the lighting apparatus. In particular, a period of operating the second light emitting diode 31 or the magnitude of the irradiance thereof may be adjusted in consideration of the hazard to the human body.

For example, the irradiance of the second light emitting diode 31 emitted from the lighting apparatus may be 1 $W/m^2$ or less, and in some exemplary embodiments, may be 0.1 $W/m^2$ or less. 1 $W/m^2$ represents a limit value of risk group 1 for blue light in a range 300 nm to 700 nm in the Photobiological Safety Standard (IEC 62471), and 0.1 W/m² corresponds to an exempt. The lighting apparatus according to an exemplary embodiment has the radiance of 1 W/m² or less, and thus, the lighting apparatus may be driven to sterilize pathogenic microorganisms for a relatively long period of time.

The sterilizing function of the lighting apparatus is described above as being exerted by the second light emitting diode 31, however, a portion of light emitted from the first light emitting diode 21 may also contribute to sterilizing pathogenic microorganisms. In particular, as shown in FIG. 5, in white light having a color temperature of 6500K, light having relatively strong irradiance intensity at a wavelength band suitable for sterilizing the pathogenic microorganisms, for example, a wavelength of about 400 nm to about 420 nm, more specifically about 405 nm, is emitted. Accordingly, when the first light emitting diode 21 emits light having the central wavelength of about 400 nm to about 420 nm, the first light emitting diode 21 may be used to sterilize the pathogenic microorganisms, and in this case, the second light emitting diode 31 may be omitted.

In addition, since white light having a color temperature lower than 6500 K also emits light having a wavelength suitable for sterilizing the pathogenic microorganisms, an illuminance of light emitted from the second light emitting diode 31 may be adjusted in consideration of the irradiance of light emitted from the first light emitting diode 21 among the white light spectrum.

According to an exemplary embodiment, the lighting apparatus is capable of sterilizing pathogenic microorganisms not only in the indoor living space but also in a space where a large number of people are active, such as an airport or a hospital, thereby preventing human infection by the pathogenic microorganisms.

Figure 6:
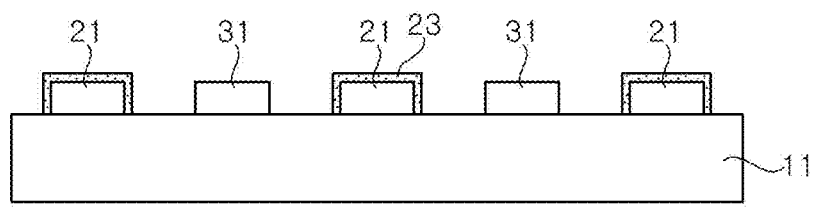
FIG. 6 is a schematic cross-sectional view illustrating a lighting apparatus according to another exemplary embodiment.

FIG. 6 is a schematic cross-sectional view illustrating a lighting apparatus according to another exemplary embodiment.

Referring to FIG. 6, the lighting apparatus according to the illustrated exemplary embodiment is generally similar to the lighting apparatus described with reference to FIG. 3 and FIG. 4, except that wavelength converters 23 are formed on the first light emitting diodes 21, respectively. More particular, the wavelength converter 23 in FIG. 3 and FIG. 4 covers all of the plurality of first light emitting diodes 21, but in the illustrated exemplary embodiment, each of the first light emitting diodes 21 is individually covered with the wavelength converter 23.

The wavelength conversion substances in the first light emitting diode 21 and the wavelength converter 23 are substantially the same as those described above, and thus, repeated descriptions thereof will be omitted.

Since the first light emitting diodes 21 are respectively covered with the wavelength converters 23, the second light emitting diode 31 may be disposed between the first light emitting diodes 21. In particular, as shown in the drawing, the second light emitting diodes 31 may be uniformly disposed between the first light emitting diodes 21, and thus, light emitted from the second light emitting diode 31 may be mixed with the white light. As such, the lighting apparatus according to an exemplary embodiment is capable of mitigating the external recognition of light emitted from the second light emitting diode 31. In some exemplary embodiments, the second light emitting diodes 31 may be covered with a transparent molding member for protection from the external environment.

According to an exemplary embodiment, the second light emitting diodes 31 may be connected in series or in parallel to the first light emitting diodes 21, but the inventive concepts are not limited thereto. For example, in some exemplary embodiments, the second light emitting diodes 31 may be mounted on the circuit board 11 to be driven independently from the first light emitting diodes 21.

In some exemplary embodiments, light emitted to the outside from the first light emitting diodes 21 may be used to sterilize pathogenic microorganisms as described above, and in this case, the second light emitting diodes 21 may be omitted.

Figure 7:
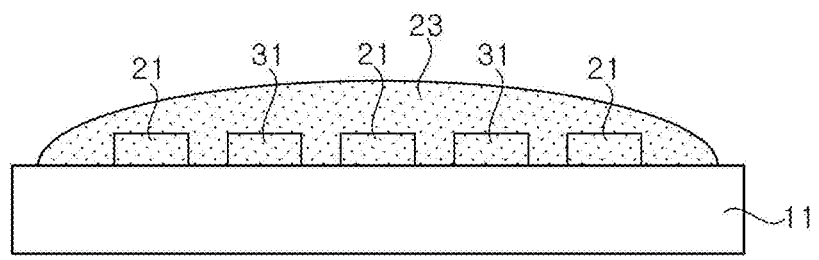
FIG. 7 is a schematic cross-sectional view illustrating a lighting apparatus according to another exemplary embodiment.

FIG. 7 is a schematic cross-sectional view illustrating a lighting apparatus according to another exemplary embodiment.

Referring to FIG. 7, the lighting apparatus according to the illustrated exemplary embodiment is generally similar to the lighting apparatus described with reference to FIG. 3 and FIG. 4, except that the second light emitting diode 31 is also covered with the wavelength converter 23.

More particularly, the wavelength converter 23 covers not only the first light emitting diode 21 but also the second light emitting diode 31. Accordingly, the wavelength converter 23 may wavelength-convert a portion of light emitted from the second light emitting diode 31.

Since the portion of light emitted from the second light emitting diode 31 is wavelength-converted by the wavelength converter 23, more second light emitting diodes 31 may be used to implement the irradiance suitable for sterilization as compared to those described above. Meanwhile, since light generated by the second light emitting diode 31 is wavelength-converted and used to implement the white light, the number of the first light emitting diodes 21 may be reduced.

The second light emitting diodes 31 may be uniformly disposed between the first light emitting diodes 21, and thus, uniform light may be emitted to the outside. However, the inventive concepts are not limited thereto.

When the first light emitting diode 21 emits light having the central wavelength in the range of 300 nm to 420 nm, the number and intensity of the second light emitting diodes 31 may be adjusted so that the irradiance of light generated by the second light emitting diodes 31 and emitted to the outside without wavelength conversion is greater than that of light generated in the first light emitting diodes 21 and emitted to the outside without wavelength conversion.

In this manner, the lighting apparatus according to the illustrated exemplary embodiment also provides an effective sterilizing function by the second light emitting diode 31.

In a particular exemplary embodiment, the first light emitting diodes 21 may emit the central wavelength in the range of about 400 nm to about 420 nm, the same as the second light emitting diode 31. Furthermore, the first light emitting diodes 21 and the second light emitting diodes 31 may emit light of the same wavelength, for example, light of 405 nm wavelength.

Figure 8:
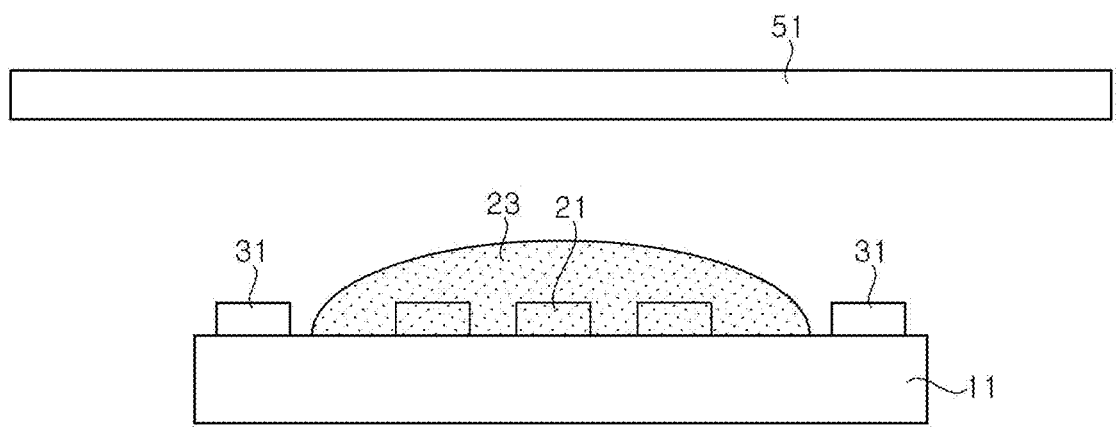
FIG. 8 is a schematic cross-sectional view illustrating a lighting apparatus according to another exemplary embodiment.

FIG. 8 is a schematic cross-sectional view illustrating a lighting apparatus according to another exemplary embodiment.

Referring to FIG. 8, the lighting apparatus according to the illustrated exemplary embodiment is generally similar to the lighting apparatus described with reference to FIG. 3 and FIG. 4, except that it further includes a diffusion plate 51.

The diffusion plate 51 may mix the white light and light emitted from the second light emitting diode 31 and provide a uniform light. Accordingly, visibility of light emitted from the second light emitting diode 31 may be reduced.

Figure 9:
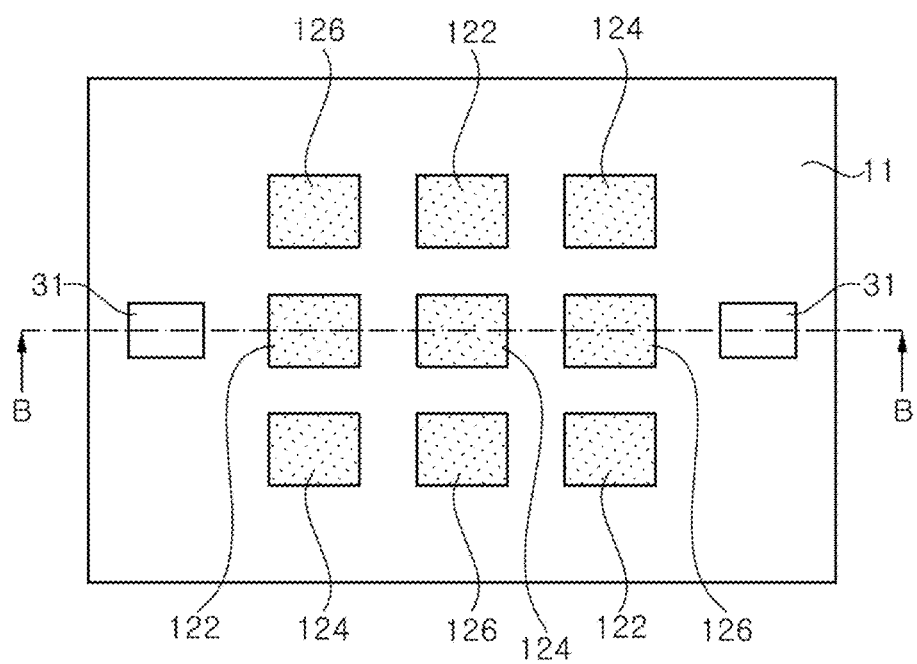
FIG. 9 is a schematic plan view illustrating a lighting apparatus according to another exemplary embodiment.
Figure 10:
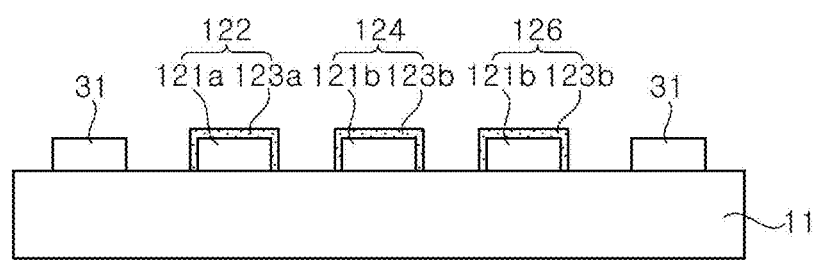
FIG. 10 is a schematic cross-sectional view taken along line B-B of FIG. 9.

FIG. 9 is a schematic cross-sectional view illustrating a lighting apparatus according to another exemplary embodiment, and FIG. 10 is a schematic cross-sectional view taken along line B-B of FIG. 9.

Referring to FIG. 9 and FIG. 10, the lighting apparatus according to the illustrated exemplary embodiment includes a substrate 11 (or a circuit board), a first light emitting unit 122, a second light emitting unit 124, a third light emitting unit 126, and a second light emitting diode 31. Since the substrate 11 and the second light emitting diode 31 are similar to those described with reference to FIG. 3 and FIG. 4, repeated descriptions thereof will be omitted to avoid redundancy.

The first light emitting unit 122 includes a first first-light emitting diode 121a and a first wavelength converter 123a, the second light emitting unit 124 includes a first second-light emitting diode 121b and a second wavelength converter 123b, and the third light emitting unit 126 includes a first third-light emitting diode 121c and a third wavelength converter 123c.

The first first- to first third-light emitting diodes 121a, 121b, and 121c may emit light having a central wavelength in a range of about 300 nm to about 420 nm, respectively. In particular, the first first- to first third-light emitting diodes 121a, 121b, and 121c may have a central wavelength in a range of about 400 nm to about 420 nm. These may be the same light emitting diodes, or may be light emitting diodes having different central wavelengths.

The first to third wavelength converters 123a, 123b, and 123c include a blue wavelength conversion substance for converting light emitted from the light emitting diode into blue light, respectively. The first to third wavelength converters 123a, 123b, and 123c may also include a green wavelength conversion substance for converting light emitted from the light emitting diode into green light, and a red wavelength conversion substance for converting light emitted from the light emitting diode into red light, respectively. The blue conversion substance, the green wavelength conversion substance, and the red wavelength conversion substance may be selected from the blue phosphor, the green phosphor, and the red phosphor described with reference to FIG. 3 and FIG. 4. In some exemplary embodiments, these phosphors may also be replaced with quantum dots.

The first to third light emitting units 122, 124, and 126 may emit white light having different color temperatures. As such, the first to third wavelength converters may include different wavelength conversion substances or different amounts of wavelength conversion substances.

In addition, the first to third light emitting units 122, 124, and 126 may be independently driven. For example, the first light emitting unit 122 may implement white light having a color temperature of 2700K, the second light emitting unit 124 may implement white light having a color temperature of 4000K, and the third light emitting unit 126 may implement white light having a color temperature of 6000K or 6500K. As such, the first to third light emitting units are selectively driven for a day, and thus, the color temperature of the lighting apparatus may be changed in accordance with the change of sunlight. In some exemplary embodiments, the first to third light emitting units 122, 124, and 126 may be driven together. White light having various color temperatures may be implemented by combining the first to third light emitting units 122, 124, and 126.

In irradiance spectrum of light emitted to the outside, irradiance of the central wavelength of light generated by each of the light emitting diodes 121a, 121b, and 121c in the first to third light emitting units 122, 124, and 126 and emitted to the outside without wavelength conversion is smaller than that of a peak wavelength of blue light emitted from the corresponding respective wavelength converters 123a, 123b, and 123c. Accordingly, the lighting apparatus according to an exemplary embodiment may not cause eye diseases or skin diseases.

The second light emitting diode 31 may be driven together when at least one of the first to third light emitting units 122, 124, and 126 is driven. In addition, the second light emitting diode 31 may be driven independently from the first to third light emitting units 122, 124, and 126, and thus, the second light emitting diode 31 may be driven even when the first to third light emitting units 122, 124, and 126 are not driven. As such, the second light emitting diode 31 may be operated to perform the sterilization even at night when the lighting apparatus is not used.

Light suitable for sterilizing pathogenic microorganisms may be emitted from the first to third light emitting units 122, 124, and 126. For example, when at least one of the first first- to first third-light emitting diodes 121a, 121b, and 121c emits light having the central wavelength of about 400 nm to about 420 nm, more particularly, light having the central wavelength of 405 nm, these light emitting units may be used to implement white light and to sterilize pathogenic microorganisms. Accordingly, in consideration of irradiance of light emitted from the first to third light emitting units 122, 124, and 126, on/off of the second light emitting diodes 31 or irradiance of light emitted from the second light emitting diodes 31 may be adjusted.

The first to third light emitting units 122, 124, and 126 may be disposed so that each of the light emitting units is evenly distributed. In the illustrated exemplary embodiment, although the second light emitting diodes 31 are shown to be disposed outside of locations where the first to third light emitting units 122, 124, and 126 are disposed, the inventive concepts are not limited thereto, and may be disposed together with the first to third light emitting units 122, 124, and 126 in some exemplary embodiments.

According to the illustrated exemplary embodiment, the first to third light emitting units 122, 124, and 126 have structures where the wavelength converters 123a, 123b, and 123c surround the light emitting diodes 121a, 121b, and 121c. These light emitting units may be chip scale packages, for example. However, the inventive concepts are not limited thereto, and in some exemplary embodiments, the light emitting units 122, 124, and 126 may be light emitting devices having the form in a conventional package well known in the art.

Figure 11:
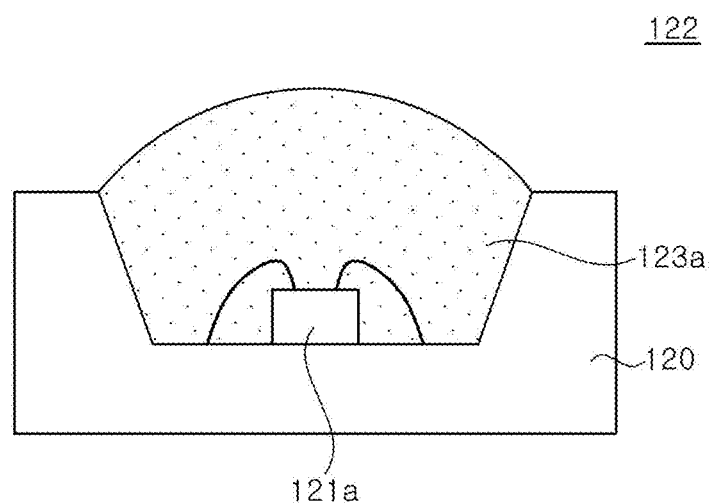
FIG. 11 is a schematic cross-sectional view illustrating a light emitting unit according to another exemplary embodiment.

FIG. 11 is a schematic cross-sectional view illustrating a light emitting unit according to another exemplary embodiment. FIG. 11 schematically shows a light emitting device in the form of a conventional package.

Referring to FIG. 11, the first light emitting unit 122 includes a first first-light emitting diode 121a and a first wavelength converter 123a. The first first-light emitting diode 121a may be mounted in a cavity of a housing 120, and the first wavelength converter 123a covers the light emitting diode 121a in the cavity. The first first-light emitting diode 121a may be electrically connected to lead electrodes through bonding wires.

The package shown in FIG. 11 is merely exemplarily, and various kinds of packages may be used. In addition, the first wavelength converter 123a may cover the light emitting diode 121a in various shapes.

Although the first light emitting unit 122 is exemplarily described herein, the second light emitting unit 124 and the third light emitting unit 126 may also have substantially the same package form as the first light emitting unit 122.

In addition, the second light emitting diode 31 may also be provided as a light emitting device in a package form and mounted on the substrate 11. However, the second light emitting diode 31 may be covered with a transparent molding member instead of being covered with the wavelength converter.

Lighting apparatuses according to an exemplary embodiment may change the color temperature of white light in response to the change in the color temperature of sunlight over time. Furthermore, the lighting apparatuses according to an exemplary embodiment may change the color temperature of white light in consideration of the change in the color temperature of sunlight according to a region.

Figure 12:
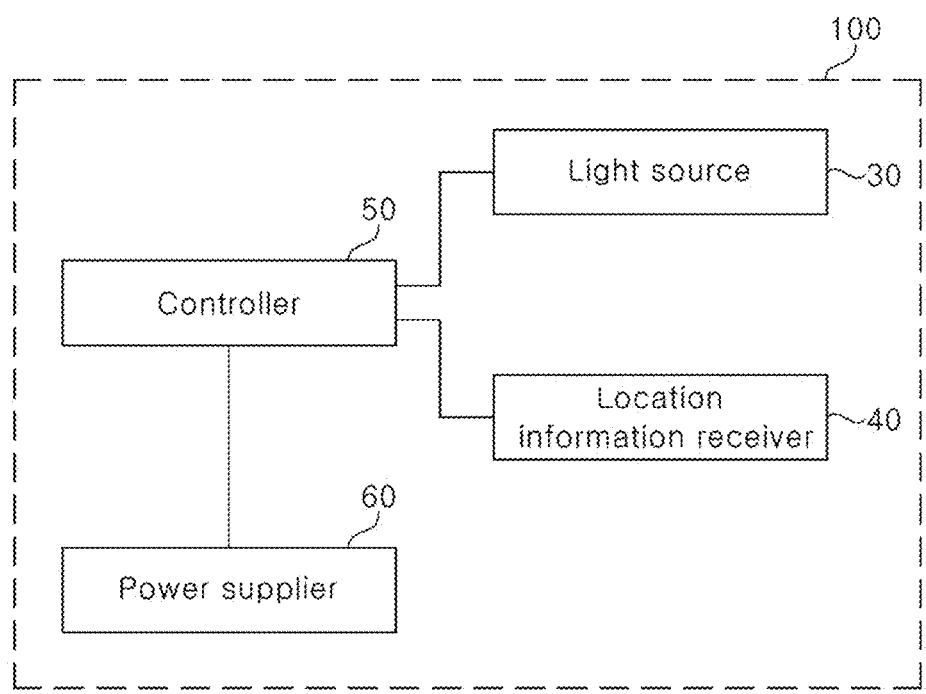
FIG. 12 is a block diagram illustrating a lighting apparatus according to an exemplary embodiment.

FIG. 12 is a block diagram illustrating a lighting apparatus 100 according to an exemplary embodiment.

Referring to FIG. 12, the lighting apparatus 100 according to an exemplary embodiment includes a light source 30 emitting light, a location information receiver 40 for receiving location information, and a controller 50 receiving the location information from the location information receiver 40 and controlling a dose of light emitted from the light source 30. As used herein, the location information refers to information that can be obtained by using a global positioning system (GPS). The light source 30 refers to a white light source that implements white light, and is an arbitrary light source capable of changing the color temperature. For example, the light source 30 may be the white light emitting device including the first light emitting diode 21 and the wavelength converter 23 or the first to third light emitting units 122, 124, and 126, without being limited thereto.

The location information receiver 40 receives the location information from a satellite using GPS to calculate current location information of the lighting apparatus 100. In particular, the location information may include latitude and longitude, and the location information, such as current latitude and longitude of the lighting apparatus 100, may be obtained from location information received by the location information receiver 40. The location information obtained by using the location information signal is provided to the controller 50.

The controller 50 calculates a dose of light to be emitted by the light source 30 based on the location information provided by the location information receiver 40, and controls the light source 30 to emit light as much as the dose of light. In other words, the controller 50 may control whether the light is emitted or not, an amount of light, an intensity of light, an emission time, and the like. The controller 50 may also control a dose of light to be emitted from the second light emitting diode 31 to sterilize pathogenic microorganisms together with the dose of the light source 30. In particular, the controller 50 may control the dose of light emitted from the second light emitting diode 31 according to the dose of the white light source 30.

The power supplier 60 is electrically connected to the controller 50 to supply power to the light source 30 and the location information receiver 40. The power supplier 60 is illustrated as suppling power to the light source 30 and the location information receiver 40 through the controller 50, but the inventive concepts are not limited thereto. For example, in some exemplary embodiments, the light source 30 and the location information receiver 40 may be directly connected to the power supplier 60, respectively.

The light source 30 and the location information receiver 40 may be disposed on the substrate 11. However, in some exemplary embodiments, the location information receiver 40 may be disposed on a substrate different from the substrate 11 on which the light source 30 is disposed.

Sunlight is not irradiated at the same intensity to all places on the earth. As the latitude becomes lower, the dose of sunlight becomes greater, and, as the latitude becomes higher, the dose of sunlight becomes less. In addition, as the altitude becomes higher, the dose of sunlight becomes greater, and, as the altitude becomes lower, the dose of sunlight becomes smaller. Accordingly, depending on which country and in which place a user of the lighting apparatus 100 is present, the time or degree of exposure to sunlight may vary.

In an exemplary embodiment, a location of the lighting apparatus 100 is determined by using location information, a dose of sunlight is calculated at the location, and then the visible light corresponding to the dose of sunlight is irradiated to a user. In this manner, the user may obtain the effect of being exposed to sunlight within a harmless limit to the human body. This will be described in more detail with reference to the drawings.

Figure 13:
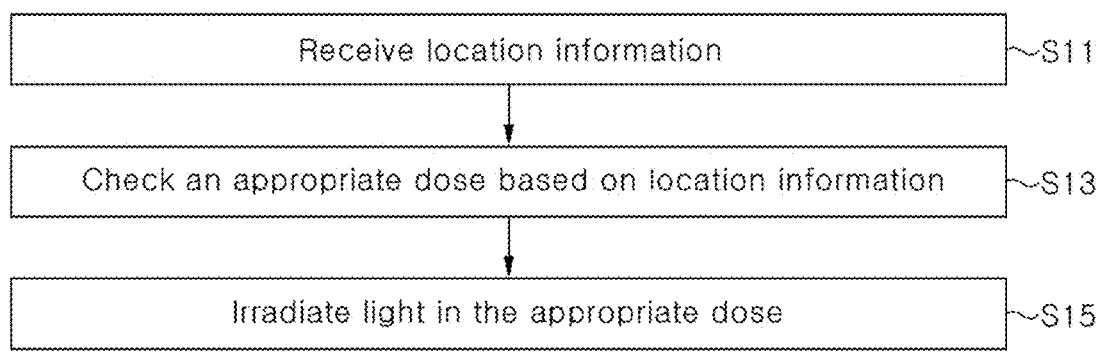
FIG. 13 is a flowchart illustrating a method of driving a light irradiation apparatus according to an exemplary embodiment.

FIG. 13 is a flowchart illustrating a method of driving a light irradiation apparatus according to an exemplary embodiment.

Referring to FIG. 13, a location information receiver receives location information (S11). For example, it may be determined that the light irradiation apparatus is located in city B of country A according to the location information obtained from the location information receiver.

The received location information is provided to a controller, and the controller checks or calculates an appropriate dose of light to be emitted by the light irradiation apparatus based on the location information (S13). For example, when city B of country A is determined, in addition to the latitude and longitude information of city B of country A, information such as sunrise time, sunset time, and average amount of sunshine may be calculated. When using the latitude and longitude information, the sunrise and sunset time on the latitude and longitude may be easily confirmed, and thus, the controller may determine whether it is a day or night using an algorithm that calculates the sunrise and sunset time on the current latitude and longitude.

Using the information such as sunrise time, sunset time, and average amount of sunshine, the controller may calculate the turn-on time, turn-off time, light intensity, etc. of the light source, so as to have a similar dose to that of the actual sunlight, that is, to have an appropriate dose. In particular, the controller may properly adjust whether the light source is irradiated or not by accurately determining the day or night light without adding an illumination sensor.

The information such as sunrise time, sunset time, and average amount of sunshine at each location may be stored in a separate memory in the controller, or may be obtained by accessing a separate internet network or the like.

The controller may control irradiation of light in a dose corresponding to the appropriate dose calculated by turning on or off the light source, to the user from the light source (S15). The user may be irradiated with the dose substantially the same as that of sunlight at the place where the user is, even if the user does not go outdoors.

According to an exemplary embodiment, even if the user is in an environment where he or she is hardly exposed to sunlight, for example, living indoors for a long time, being in a hospital room or a limited space, or mainly being active at night, light similar to sunlight at the present location may be provided in an appropriate dose for a suitable time. Accordingly, the user may be in a familiar environment, psychological stability of the user may be possible, and the irradiation time may also be controlled by setting the sunrise or sunset time, thereby easily recovering the daily biorhythm.

In the exemplary embodiment described above, although it has been described that a single light is used instead of sunlight based on the location information, the inventive concepts are not limited thereto. The light irradiation apparatus may be used as a correction light source that compensates for a lack of external light in the presence of natural light, e.g., external light emitted from sunlight or lighting apparatuses. For example, in a place with high latitude, the amount of sunshine may be significantly lower than in a region with low latitude, in which case it may be necessary to compensate for the lack of sunshine. When the amount of sunshine is low, not only light in the visible light wavelength band irradiated to the user may be insufficient, but also light in the ultraviolet light wavelength band may be insufficient. In this case, the light irradiation apparatus according to an exemplary embodiment may compensate for the insufficient light by additionally irradiating light of the visible light wavelength band and light of the ultraviolet wavelength band.

Figure 14:
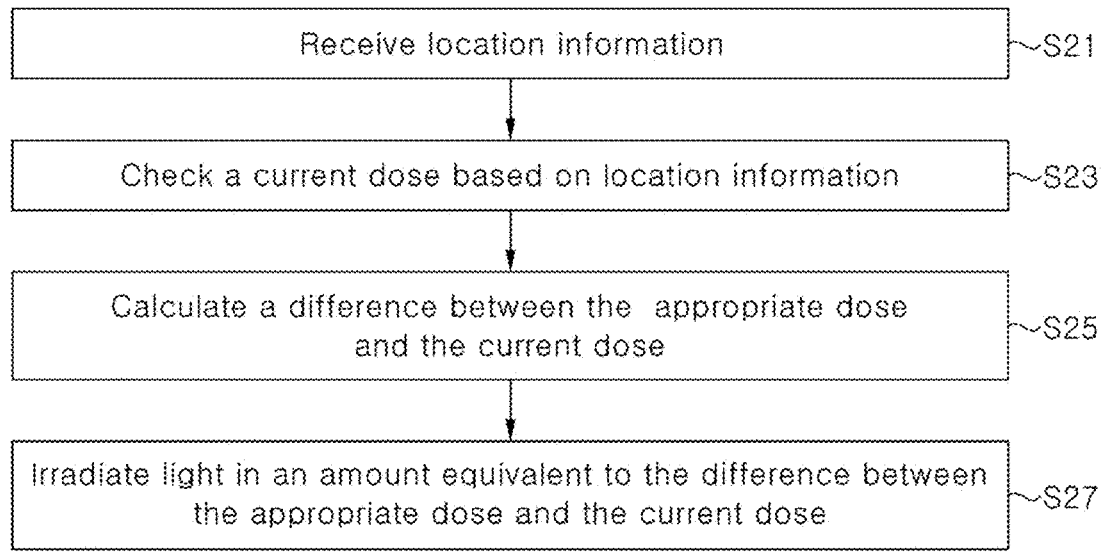
FIG. 14 is a flowchart illustrating a method of driving the light irradiation apparatus according to an exemplary embodiment.

FIG. 14 is a flowchart illustrating a method of driving the light irradiation apparatus according to an exemplary embodiment.

Referring to FIG. 14, a location information receiver receives location information (S21). For example, it may be determined that the light irradiation apparatus is located in city D of country C according to the location information obtained from the location information receiver.

The received location information is provided to a controller, and the controller calculates information such as sunrise time, sunset time, and average amount of sunshine at a current location based on the location information, and, using the information such as sunrise time, sunset time, and average amount of sunshine, calculates a current dose of actual sunlight (S23).

Next, a difference between an appropriate dose required for the user and the current dose is calculated (S25). For example, in the case of city D of country C, which is located in a region with high latitude and an amount of sunshine is insufficient, an amount of sunshine actually required is the appropriate dose, and a value obtained by subtracting the current dose from the appropriate dose is an insufficient dose. The appropriate dose required for the user may be stored in a separate memory or the like in the controller, or may be obtained by connecting to a separate internet network or the like.

The controller may then cause irradiation of light in a dose corresponding to the difference between the appropriate dose calculated by turning on or off the light source and the external light dose, that is, light with the insufficient dose, to a target object from the light source (S27).

The user may be irradiated with the predetermined light in the dose most appropriate to the user based on the user's location.

Although various lighting apparatuses have been described above, the inventive concepts are not limited thereto. In addition, the lighting apparatus may be installed in not only an indoor living space but also an indoor space used by a plurality of people, such as a hospital or an airport.

Thus, a lighting system, in which the lighting apparatus is installed, may also be provided, which may be suitable for routinely sterilizing pathogenic microorganisms, and may operate the lighting apparatus to effectively sterilize pathogenic microorganisms even when people are inactive.

Figure 15A:
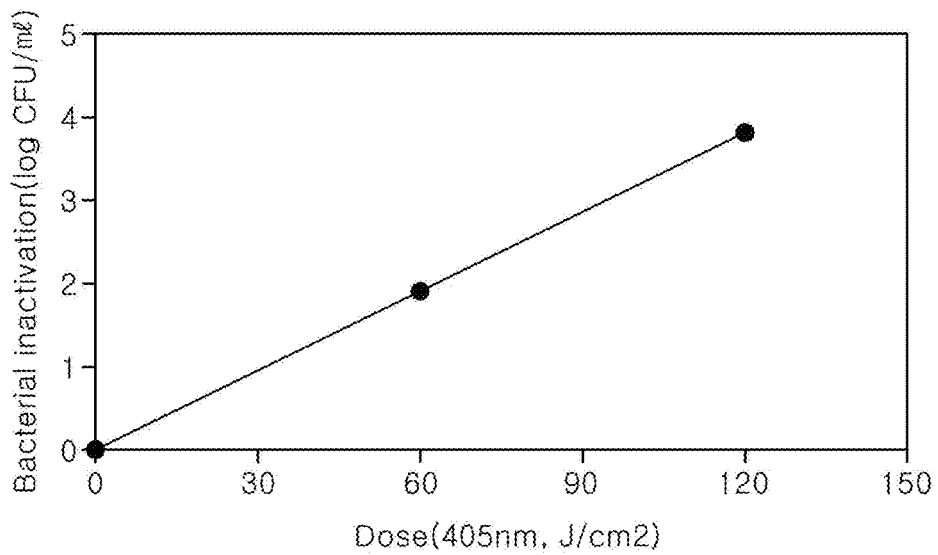
FIG. 15A and FIG. 15B are graphs illustrating results of sterilization experiment on *Escherichia coli* and *Staphylococcus aureus* according to doses of light of a second light emitting diode.
Figure 15B:
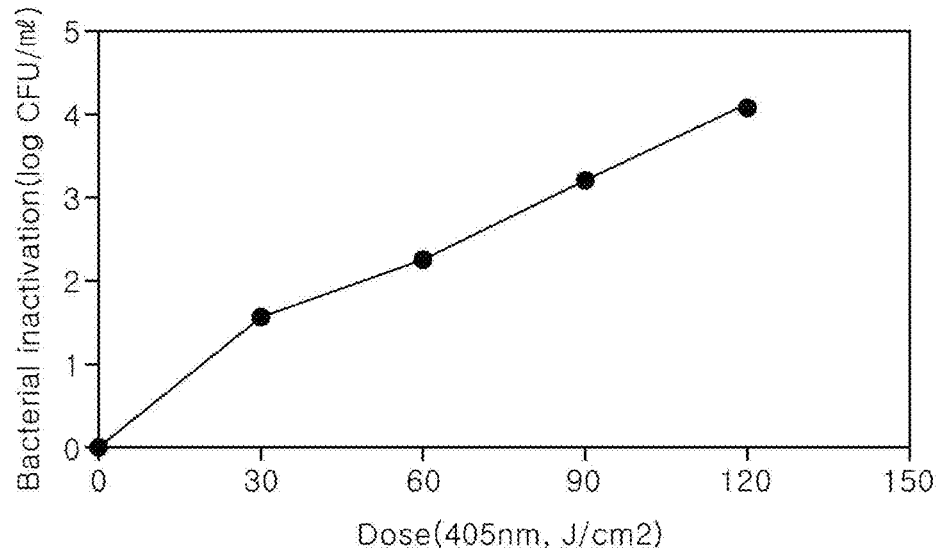

FIG. 15A and FIG. 15B are graphs illustrating results of sterilization experiment on *Escherichia coli* and *Staphylococcus aureus* according to doses of light of a second light emitting diode, and FIG. 13 shows photographs showing the result of sterilization experiment on *Escherichia coli* cultured in the medium according to the doses of light of the second light emitting diode. As the second light emitting diode, a light emitting diode having a central wavelength of 405 nm was used.

Each bacterium was plated in a bacterial culture medium and incubated at 35-37° C. for one day. Colonies formed on the culture medium were collected and clouded in physiological saline and centrifuged, after discarding a supernatant. Physiological saline was added again to prepare a bacterial solution, and the bacterial solution was diluted to prepare a bacterial solution of a suitable concentration for the sterilization experiment.

After installing a sterilizing light source at a specific distance from the container containing the bacterial solution, the bacterial solution was irradiated with light, and, to confirm the sterilization power from the irradiated bacterial solution, the bacterial solution was diluted and evenly applied onto the medium and then incubated at 35-37° C. for one day.

The colonies formed on the bacterial culture medium were identified and multiplied by a dilution factor and counted.

Graphs in FIG. 15A and FIG. 15B show the sterilization power according to the doses of light compared to the control bacteria without the sterilizing light source installed. It can be confirmed that the sterilization capability on the pathogenic microorganism increases as the dose of light increases. As used herein, numeral number one (1) on the y-axis denotes 90% sterilization power, numeral number two (2) denotes 99% sterilization power, and numeral number three (3) denotes 99.9% sterilization power. As such, it can be seen that the dose of light in a range of about 20 J/cm$^2$ to about 30 J/cm$^2$ shows the sterilization power of about 90%, the dose of light in a range of about 50 J/cm$^2$ to about 60 J/cm$^2$ shows the sterilization power of about 99%, and the dose of light in a range of about 80 J/cm$^2$ to about 95 J/cm$^2$ shows the sterilization power of about 99.9%.

Figure 16:
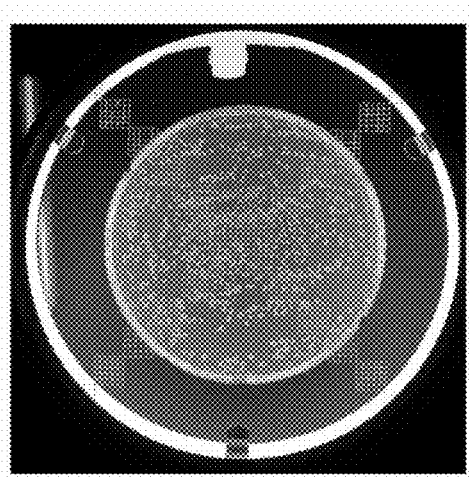
FIG. 16 shows photographs showing the result of sterilization experiment on *Escherichia coli* cultured in the medium according to doses of light of the second light emitting diode.
Figure 16:
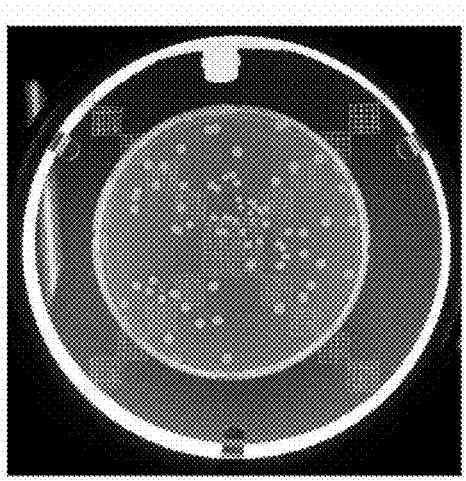
Figure 16:
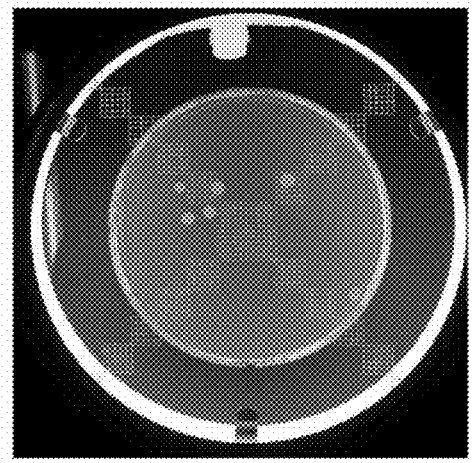
Figure 16:
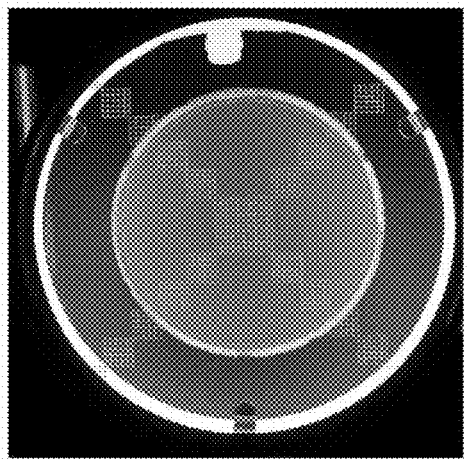

In addition, referring to FIG. 16, as the dose of light increases, the number of bacteria decreases, and it can be seen that a size of the colony increases as the number of bacteria decreases. Meanwhile, when the dose of light further increases, the bacteria are almost eliminated and not observed.

Meanwhile, Table 1 below shows relative intensities, relative light doses, and relative sterilization powers of the 405 nm wavelength according to color temperatures of the white light source, which are derived using the spectrum (FIG. 2) of conventional light sources (comparative example) and the spectrum (FIG. 5) of light sources (exemplary embodiment).

TABLE 1

| Color | % Intensity (@405 nm) | | Relative Light Dose (J/cm$^2$) | | Relative Sterilization Power | | | |
|---|---|---|---|---|---|---|---|---|
| | | | | | E. coli | | S. aureus | |
| | Exem. Embodiment | Comp. Example | Exem. Embodiment | Comp. Example | Exem. Embodiment | Comp. Example | Exem. Embodiment | Comp. Example |
| 6500K | 100 | 7.75 | 90 | 7 | 100 | 8.01 | 100 | 14.58 |
| 5000K | 40.9 | 14.62 | 37 | 13 | 41.1 | 14.87 | 45.3 | 20.94 |
| 4000K | 46.5 | 14.25 | 42 | 13 | 46.6 | 14.49 | 50.4 | 20.59 |
| 3000K | 28.3 | 4.24 | 26 | 4 | 28.5 | 4.52 | 33.6 | 11.33 |

Referring to Table 1, it shows that the intensity at the wavelength of 405 nm of the light source of the exemplary embodiment having the color temperature of 6500K is the largest, and that of the light source of the exemplary embodiment having the color temperature of 3000K is relatively small. Meanwhile, the light source of the comparative example shows a very small intensity even at the color temperature of 6500K and shows a smaller intensity than that of the light source of the exemplary embodiment having the color temperature of 3000K at all color temperatures.

When a dose of light of the 6500K light source among the light sources of the embodiment is 90 J/cm$^2$, light doses of the different light sources under the same condition are listed together in the table. Among the light sources of the exemplary embodiments, the light sources having the color temperature of 5000K or less showed doses of light smaller than ½ of the dose of light having the color temperature of 6500K. Meanwhile, the light sources of the comparative example show a light dose smaller than that of 3000K in the exemplary embodiment.

For the sterilization power on *E. coli* and *Staphylococcus aureus* (*S. aureus*), the sterilization powers of other light sources at the same irradiation time are listed in the table as relative values, when the sterilization power of the light source having the color temperature of 6500K among the light sources of the exemplary embodiment is 100%. As shown in Table 1, it can be seen that the light source of the embodiment shows a relatively strong sterilization power at the color temperature of 6500K.

Although some exemplary embodiments have been described herein, it should be understood that these embodiments are provided for illustration only and are not to be construed in any way as limiting the present disclosure. It should be understood that features or components of one exemplary embodiment may also be applied to other exemplary embodiments without departing from the spirit and scope of the present disclosure.

What is claimed is:

1. A light emitting apparatus, comprising:
   a substrate;
   a first light emitter disposed on the substrate and including at least one first light emitting diode and a wavelength converter;
   a second light emitter disposed on the substrate and spaced apart from the wavelength converter; and
   a controller configured to control at least one of the first light emitter or the second light emitter,
   wherein:
   the first light emitting diode is configured to emit a primary light having a peak wavelength in a range of violet or blue light;
   the wavelength converter includes wavelength conversion materials that convert the primary light to light having a peak wavelength in a green or red light wavelength range;
   the first light emitter emits a first light and the second light emitter emits a second light;
   the second light has a peak wavelength different from the peak wavelength of the primary light; and
   an irradiance of the peak wavelength of the second light is configured to be greater than that of the first light at the same wavelength.

2. The light emitting apparatus of the claim 1, wherein the controller controls a driving time of the first light emitter and the second light emitter.

3. The light emitting apparatus of claim 2, wherein the driving time of the second light emitter and that of the first light emitter are the same.

4. The light emitting apparatus of claim 1, wherein the light emitting apparatus emits a third light generated by the first light and the second light to an outside of the light emitting apparatus.

5. The light emitting apparatus of claim 4, wherein in the third light, an irradiance of the second light is different from an irradiance of the first light.

6. The light emitting apparatus of claim 5, wherein in the third light, an irradiance of the peak wavelength of the second light is greater than an irradiance of the peak wavelength of the first light.

7. The light emitting apparatus of claim 1, wherein the light emitting apparatus comprises a different number of first light emitters and second light emitters.

8. The light emitting apparatus of claim 7, wherein the second light emitter is disposed between a plurality of the first light emitters.

9. A light emitting apparatus, comprising:
   a substrate;
   a first light emitter disposed on the substrate and including at least one first light emitting diode and a wavelength converter;
   a second light emitter disposed on the substrate and spaced apart from the wavelength converter; and
   a controller configured to control at least one of the first light emitter or the second light emitter,
   wherein:
   the first light emitting diode is configured to emit a primary light having a peak wavelength in a range of violet or blue light;
   the wavelength converter includes wavelength conversion materials that convert the primary light to light having a peak wavelength in a green or red light wavelength range;
   the first light emitter emits a first light and the second light emitter emits a second light;

the second light has a peak wavelength different from the peak wavelength of the primary light;

the light emitting apparatus is configured to emit a third light generated by the first light and the second light to an outside of the light emitting apparatus; and in the third light, an irradiance of the peak wavelength of the second light is configured to be greater than that of the first light at the same wavelength.

10. The light emitting apparatus of claim 9, wherein the controller controls a driving time of the first light emitter and the second light emitter.

11. The light emitting apparatus of claim 10, wherein the driving time of the second light emitter is different from that of the first light emitter.

12. The light emitting apparatus of claim 9, wherein the light emitting apparatus comprises a different number of first light emitters and second light emitters.

13. The light emitting apparatus of claim 12, wherein the second light emitter is disposed between a plurality of the first light emitters.

14. The light emitting apparatus of claim 9, wherein in the third light, an irradiance of the peak wavelength of the second light is configured to be different from an irradiance of light generated by the first light emitting diode and emitted to the outside without wavelength conversion by the wavelength converter.

15. A light emitting apparatus, comprising:
a substrate;
a first light emitter disposed on the substrate and including at least one first light emitting diode and a wavelength converter;
a second light emitter disposed on the substrate and spaced apart from the wavelength converter; and
a controller configured to control at least one of the first light emitter or the second light emitter,
wherein:
the first light emitting diode is configured to emit a primary light having a peak wavelength in a range of violet or blue light;
the wavelength converter includes wavelength conversion materials to convert the primary light to light having a peak wavelength in a green or red light wavelength range;
the first light emitter emits a first light and the second light emitter emits a second light;
the second light has a peak wavelength different from the peak wavelength of the primary light;
the light emitting apparatus is configured to emit a third light generated by the first light and the second light to an outside of the light emitting apparatus; and
in the third light, an irradiance of the peak wavelength of the second light is configured to be different from an irradiance of light generated by the first light emitting diode and emitted to the outside without wavelength conversion by the wavelength converter.

16. The light emitting apparatus of claim 15, wherein in the third light, an irradiance of the second light is different from an irradiance of the first light.

17. The light emitting apparatus of claim 16, wherein in the third light, an irradiance of the peak wavelength of the second light is greater than an irradiance of the peak wavelength of the first light.

18. The light emitting apparatus of claim 15, wherein in the third light, the irradiance of the peak wavelength of the second light is greater than that of the first light at the same wavelength.

19. The light emitting apparatus of claim 15, wherein the second light is emitted to the outside of the light emitting apparatus without passing through the wavelength converter.

20. The light emitting apparatus of claim 15, wherein the second light emitter is exposed from the wavelength converter.

* * * * *